(12) United States Patent
Dingeldein et al.

(10) Patent No.: US 8,003,121 B1
(45) Date of Patent: Aug. 23, 2011

(54) MODULAR IMPLANT SYSTEM CONTAINING ACTIVE SUBSTANCES AND METHOD FOR THE PRODUCTION THEREOF

(75) Inventors: Elvira Dingeldein, Dreieich (DE); Helmut Wahlig, Darmstadt (DE); Jörg Bauer, Darmstadt (DE); Edgar Wüst, Rodgau (DE); Christoph Sattig, Dieburg (DE)

(73) Assignee: aap Biomaterials GmbH & Co. KG, Dieberg (DE)

( * ) Notice: Subject to any disclaimer, the term of this patent is extended or adjusted under 35 U.S.C. 154(b) by 153 days.

(21) Appl. No.: 10/343,363

(22) PCT Filed: Aug. 1, 2000

(86) PCT No.: PCT/EP00/07426
§ 371 (c)(1),
(2), (4) Date: Jan. 30, 2003

(87) PCT Pub. No.: WO02/09783
PCT Pub. Date: Feb. 7, 2002

(51) Int. Cl.
*A61L 24/00* (2006.01)
*A61L 24/06* (2006.01)

(52) U.S. Cl. ..... 424/423; 424/422; 424/487; 623/16.11; 522/184

(58) Field of Classification Search .......... None
See application file for complete search history.

(56) References Cited

U.S. PATENT DOCUMENTS

| | | | |
|---|---|---|---|
| 3,917,628 A * | 11/1975 | Vanhoof et al. | 546/282.4 |
| 4,059,684 A | 11/1977 | Gross et al. | |
| 4,808,228 A * | 2/1989 | Randklev | 106/35 |
| 5,650,108 A * | 7/1997 | Nies et al. | 264/122 |
| 2001/0051187 A1* | 12/2001 | Yang | 424/489 |

FOREIGN PATENT DOCUMENTS

| | | |
|---|---|---|
| DE | 207 655 | 3/1984 |
| DE | 35 42 972 A1 | 6/1987 |
| DE | 44 33 201 A1 | 3/1996 |
| DE | 44 35 680 A1 | 4/1996 |
| DE | 25 11 122 B2 | 6/1997 |
| DE | 196 41 775 A1 | 2/1998 |
| DE | 197 13 229 A1 | 10/1998 |
| DE | 19713229 A1 | 10/1998 |
| DE | 19918295 A1 | 10/2000 |
| EP | 0701824 A2 | 3/1996 |
| EP | 0702966 A2 * | 3/1996 |
| WO | 9301841 A1 | 2/1993 |

OTHER PUBLICATIONS

Scott et al. "Effectiveness of Bone Cement Containing Trobacyin". J Bone Joint Surg 1999.*
Press Release Stryker 2008. (see attached document) also available at www.strykercorp.com.*

* cited by examiner

*Primary Examiner* — Robert A Wax
*Assistant Examiner* — Danah Al-Awadi
(74) *Attorney, Agent, or Firm* — Norris, McLaughlin & Marcus, P.A.

(57) ABSTRACT

System of implant components containing active agents, wherein each component is intended to function as an additive for an implant material produced with a powdery or finely granulated starting material and/or active agents and additives.

Each component is powdery or finely granulated and includes at least one powdery or finely granulated active agent or additive having a higher dosage than the desired concentration for the application. The components themselves are made of a powdery or finely granulated starting material for the implant material, as well as of the active agent or additive. The active agents can be chemotherapeutical agents, such as antibiotics, whereas the additives can be x-ray contrast materials and/or or additives that alter the physical properties of the starting material, such as its elasticity or viscosity.

20 Claims, No Drawings

MODULAR IMPLANT SYSTEM CONTAINING ACTIVE SUBSTANCES AND METHOD FOR THE PRODUCTION THEREOF

The invention relates to a modular implant system for producing an implant material with a basic component containing powdery or granular polyacrylates and/or polymethacrylates and at least one implant component containing one or more active agents and or additives, in particular for bone cements, immediately before their use, for application in orthopedic surgery and traumatology.

Since many years, replacing diseased, painful and no longer functional joints with artificial implants is known in the art. In particular, a total hip joint replacement is one of the most successful and cost-effective surgical procedures in this field.

Essentially two methods exist for anchoring the joint prostheses in the bone structure. Firstly, the prosthesis components can be fixed in the bone by a pure press fit without the use of additional materials. Secondly, the prosthesis parts can be embedded in a plastic material previously introduced into the bone space, whereby the plastic material hardens through polymerization in the bone support, thereby permanently fixing and anchoring the prosthesis in the bone.

It is estimated that over one million hip joint replacement operations are performed worldwide every year. Although more than 90% of the implanted prostheses have a useful life in excess of 10 years, the sheer number of procedures results in a not insignificant number of complications. Aseptic loosening, deep infections and technical mistakes are complications which most frequently make replacement operations (revisions) necessary. This observation is based on results from the Swedish National Register which lists the number of revised total hip arthroplasties performed from 1979 to 1990 with a 10-year follow-up, showing a total of 92,675 primary total hip endoprosthesis operations and a rate of 4858 first revisions (Malchau et al., Institute for Orthopedics of the University Gothenburg, Sweden: "Prognosis for the Total Hip Arthroplasty", Annual Meeting of the American Academy of Orthopedic Surgeons, Feb. 18-23, 1993, San Francisco, USA). Based on this study, 79% of the 4858 first revisions were caused by aseptic loosening, 9.7% caused by deep infections and 5.9% due to technical mistakes (other causes were 5.4% combined).

Infections are the second most frequent cause for revisions with a contribution of approximately 10% and therefore play a significant role. This is even more serious since treatment and/or repair of infected endoprostheses poses a significantly greater problem for the surgeon, the patient is under greater stress, the duration of the treatment can be quite long and the costs can be significantly higher than for revision operations caused by aseptic loosening. Accordingly, there is a great need to attack the infections prophylactically and therapeutically.

Based on an idea by Buchholz, the antibiotic agent gentamycin is commonly added to bone cement, both to prophylactically prevent deep infections from developing as well as to repair the infected joints of prostheses that were infected during revision operations by utilizing such antibiotic-containing cement.

A gentamycin-containing bone cement based on polymethylmethacrylate (Reffobacin®-Palacos® R) has been successfully used since more than 20 years in clinical applications. During this time, many experimental, pharmacokinetic and clinical investigations have proven the effectiveness of the gentamycin-PMMA-cement (e.g. Malchau et al., above).

The application of the gentamycin-containing cement as preventive measure against the deep infections has proven to be highly effective, with a significant decrease in the frequency of infections.

Based on numerous investigations, gentamycin appears to be particularly advantageous for the combination with a PMMA bone cement for bacteriological and chemical-physical reasons: gentamycin has a comparatively broad antibacterial spectrum of activity, is sufficiently heat-resistant and is released from the cement matrix in sufficient quantities.

Nonetheless, the known bone cement-gentamycin mixture still has significant disadvantages. Firstly, this product—as applied today in clinical settings—has a fixed combination of the polymer powder with only a single antibiotic, namely gentamycin, in only a single dose of 1.25 wt. % referenced to the polymer powder. Practical applications have shown that this dosage is frequently inadequate for obtaining the desired clinical effect. This applies not only to the prophylactic application, but in particular also to the application of this product in revision operations. These mostly relate to chronic etiologic processes, sometimes after several pretreatments, and infections caused by the first procedure. Infections are most frequently caused by germs (often resistant hospital germs) which enter the surgical wound during surgery, i.e., when the endoprosthesis is inserted, and settle on the metal and plastic parts of the prosthesis. It has been observed that the responsivity of such germs, after they have settled on the implants, to different antibiotics is significantly reduced as compared to identical germs in the original population in suspension.

As a second disadvantage, the gentamycin-containing cement increases the resistance of the aetiological agents to gentamycin, in particular in hospitals. However, over the last few years, the spectrum of agents causing such infections has shifted to coagulase-negative staphylococci which have assumed a greater clinical importance, since the majority of them is multi-agent-resistant and hence also gentamycin-resistant, i.e., outside the spectrum of activity of gentamycin. In addition, anaerobics, in particular anaerobic cocci, have been increasingly detected when hip endoprostheses become infected. These are germs that are also less receptive to and even essentially resistant to gentamycin.

In view of the seriousness of the clinical picture of a deep infection, the severe health risk for the patient and the socio-economical significance of this disease, there is an urgent need for optionally increasing the dose of the antibiotic, and for having available antibiotics other than gentamycin with more specificity that can be used for a targeted attack on the aetiological agents according to the determined antibiogram and their responsivity to antibiotics. In other words, using a gentamycin-containing cement, in particular with a predetermined invariable, fixed reagent concentration, does no longer satisfy the actual chemotherapeutical requirements under today's clinical conditions. Disadvantageously, commercially available gentamycin-containing bone cement can therefore no longer meet the continuously changing specific problems in various hospitals and with specific patients. This can lead to serious therapeutic disadvantages.

Moreover, commercially available cements disadvantageously can also not be physically adapted to the particular requirements associated with different clinical pictures of different patients.

New cements or modern application systems have been developed mainly for obtaining cements with adequate mechanical properties. The mechanical parameters are used for validating a sufficiently long service life of the prostheses. Neither the different prostheses materials and their modulus of elasticity, nor the shapes of the prostheses are taken into consideration. The mechanical properties of the cements are also not matched to the different bone quality and implantation situation of the individual patient. No bone cement is known to this day which is specifically adapted to the age- or disease-related changes in the bone structure (bone density). A surgeon would otherwise be able to select a suitable cement and/or assemble a specific composition of the implant mass from particularly suited components immediately before application, wherein the cement is individually formulated depending on the patient's diagnosis. According to the invention, such cement can have variable properties, e.g., relating to its processing characteristics (low, high viscosity) or elasticity (adaptation of the elasticity of the cement to the implant components), or the x-ray density (adaptation to the bone density of the patient), or the physiological organ structure of the patient (normal bone, osteoporotic bone, rheumatoid bone structure).

Such adaptation of the cement, both with respect to the addition of pharmaceutical reagents and to its mechanical properties, is urgently needed to significantly improve today's therapeutic practice and to make clinical-therapeutic treatments more successful.

Today's commercially available bone cements are very similar in their chemical composition as well as in their physical properties. Although the pathological conditions and therapeutic requirements can be satisfied for some patients, the specific therapeutic requirements can disadvantageously not be met for a majority of the patients. While a certain cement may be able to successfully anchor a specific prosthesis under normal bone conditions as encountered in younger or middle-aged patients, the same cement may not be as efficient with osteolytic processes, eburnated or osteoporotic bones, because the mechanical conditions of the bone support are here significantly different from those of "normal" bones.

A gentamycin-containing cement may be very effective in repairing bone infections caused by germs that respond to gentamycin. However, this cement cannot function in all those situations where the infection is caused by germs resistant to gentamycin. Cements with a predetermined physical potency and a fixed supply of antibiotics can therefore not be targeted for specific therapeutic applications. On the other hand, a cement produced with variable physical properties and/or a variable combination of pharmaceutical reagents would be able to reliably solve the different therapeutic problems caused by variability in the patient characteristics.

It is therefore an object of the invention, to be described hereinafter, to obviate the deficiencies of a static system by enabling an individual treatment of patients. It is another object of the invention to individually apply different pharmaceutical agents, in particular antibiotics, at different dosage and/or in combination with a predetermined implant material, to simplify and improve the application, and to apply a ready-made implant material which satisfies the rigorous clinical and pharmaceutical standards with respect to sterility, homogeneous distribution of the agents, a standardized, reproducible and protracted release of the agents, while retaining to the greatest possible extent the mixing characteristic and the mechanical properties of the material.

The implant material should also be configured on a case-by-case basis and depending on the clinical-therapeutical requirements so that a surgeon can freely select the elasticity or the viscosity of the implant material based on individual patient parameters, for example the x-ray contrast.

This object is solved by the invention based on a modular implant system of the aforedescribed type in that the implant component(s) that contain(s) the active agent(s) or additive(s) is/are also powdery or finely granular and include(s) at least one powdery or finely granular agent or additive in a higher dosage than the desired concentration for the application and has a chemical composition similar or identical to that of the basic component.

The surgeon can then decide immediately before application to flexibly combine in form of a modular system two or more different implant components to form an implant material which can thereby be adapted to the prevailing surgical conditions and the specific requirements of the patient to be treated.

Advantageously, the entire system of modular components includes the modular implant components to be described below which include a first basic implant material and additional, i.e., second, third, etc. modular components which depending on the respective application, are processed into the implant material individually or in combination with the first basic component.

The first basic implant component (1) consists of a suitable plastic material, preferably polyacrylate and/or polymethacrylate and/or co-polymers. The implant material is preferably a bone cement. Conventional bone cements are prepared by mixing approximately two parts of a fine-particle pre-polymer, which contains a polymerization catalyst (e.g. dibenoxylperoxide), in particular polymethacrylate or a mixed polymer made of methacrylate and methylmethacrylate, with one part of a liquid monomer, e.g., acrylic acid or methacryl acid methyl ester or mixtures thereof, which contains an accelerator (e.g. dimethyl-p-toluidin), into a malleable mass, which is then implanted in the body where it hardens. Such bone cements are commercially available, for example, under the trade names Palacos®, Sulfix 60®, CMW Bone Cement®, etc.

The first modular implant component of a conventional bone cement is provided in various quantities corresponding to the additional modules, wherein powdery quantities of preferably 20, 40, 60 or 80 grams in total weight are produced after mixing one or several different modular implant components with the basic component. The first modular implant component can already contain a certain amount of additives, for example an x-ray contrast material, as a basic building block. It can also contain a basic quantity of a pharmaceutically active agent, for example for basic prophylaxis. When a total hip joint endoprosthesis is implanted, a quantity can be provided as part of the basic implant component, depending on the intended application, that only treats the prosthesis shaft, or for implanting the shaft and cup or, for a revision operation.

Accordingly, a basic component of polyacrylates and/or polymethacrylates which is in powdery or granular form and an implant component of one or more active agents and/or additives, which are also in powdery or granular form, is provided, wherein the implant component includes at least one powdery or finely granular agent or additive in a higher dosage than the desired concentration for the application and has a chemical composition similar or identical to that of the basic component.

A second modular implant component (2) consists of the matrix of the first modular implant component or another implant material and an x-ray contrast material which is patient-specific. A weak x-ray contrast material or a smaller quantity of x-ray contrast material can be used for osteoporotic bones (in particular present in older female patients). A strong contrast material or a contrast material in high concentration can be used for treating young, vigorous patients with normal bone density who suffer, for example, from a fractured neck of the femur resulting from a sports injury. By specifically adapting the cement to the bone conditions, the bone cement can be reliably viewed in an x-ray image so that the healing progress can be monitored using x-rays. In another modification, the hardness of the x-ray contrast material can be specified. For example, in one practice, a soft, round grain with a low grain size distribution can be used which is particularly suitable for use with soft titanium prostheses. In another practice, a harder grain with rounded corners can be used which is better suited for cobalt-chromium-molybdenum prostheses. In still another modification, a liquid x-ray contrast material, fine metal power, preferably tantalate spheres or bioactive substances, such as for example hydroxyl apatite, may be employed.

A third modular implant component (3) consists of the matrix of the first modular implant component or another implant material and one or several pharmaceutical reactive agents.

In a preferred embodiment of the invention, the active agent(s) and/or additive(s) is/are contained in a higher concentration, at least twice the concentration, than the desired application concentration, or at least at a 30% higher concentration.

With the third modular implant component, pharmaceutical active agents, in particular antibiotics, such as gentamycin, clindamycin, erythromycin, vancomycin, teichoplanin, or in general amino glycoside, cephalosporin, penicillin, gyrase inhibitors, rifampicin or others, cytostatics, inflammation inhibitors or the like, or so-called growth factors or growth regulators are mixed in a significantly higher dose than required for the final clinical application concentration, preferably with at least one dry powdery or finely granulated basic material, for example the first basic implant component 1 or another implant material. This can be the polymer powder of a bone cement based on polyacrylates and/or polymethacrylates.

The invention has another advantage in that by applying the modular implant component 3, the quantity of active agents, for example of antibiotics, in the finished implant material can be selected freely and adapted to the clinical setting. In addition, the most suitable antibiotics can be selected based on a corresponding bacteriological preliminary examination, such as the antibiogram, or even a combination of two or antibiotics can be applied. In the context of the present invention, combinations of antibiotics with implant components, that are configured according to the implant component 3, play an important role in clinical applications. It is also possible to suitably mix separate components of one or more antibiotics with a starting implant material, for example the first modular implant component or any other combination of implant materials or a bone cement. On the other hand, according to the invention, one or more antibiotics can advantageously be mixed or combined in an implant component. Moreover, antibiotics can advantageously be selected for creating a combination that exhibits a synergistically enhanced antibacterial activity. Finally, varying the antibiotics reduces the risk of introducing resistant hospital germs. According to another feature of the invention, modifications can be used that contain only slightly soluble substances with a delayed release from the cement matrix and are active for a longer time. Other modifications may contain readily soluble components with a short-term activity and a high concentration of immediately available active agents.

Other pharmaceutical active agents or additives can be employed in addition to antibiotics. This can enable different therapeutic and prophylactic applications for the invention.

A fourth modular implant component (4) consists of a modification of polymer components whereby the modulus of elasticity of the end product representing the bone cement can be altered, for example through mixing with the first implant component. In this way, the flexibility of the bone cement can be substantially matched to the flexibility of the bone.

A fifth modular implant component (5) consists of a modification of polymer components which are specifically differentiated in their swelling characteristic and which can be mixed, for example, with the implant component 1 or with another implant material. Bone cements with different viscosities can be obtained by adjusting the mixing ratio. For example, a palette of available cements can include cements with a low viscosity, with an intermediate viscosity and with a high viscosity. The surgeon has then the option to adjust the optimal viscosity of the cement to be applied patient-specific on a case-by-case basis.

Modifications of this type can also affect the hardening time of the cement. This also allows changes in the processing time and processing latitude of the cement, which can thereby be targeted for the specific surgical and/or patient situation.

A sixth modular implant component (6) consists of the monomer that is needed for preparing the different mixtures of the modular implant components and for polymerization, with the addition of certain amount of starter materials and stabilizers. The required quantities of the monomer depend on the total amount of material made up by the different components. With a conventional mixing ratio of 2:1, for example, 10, 20, 30 or 40 ml of the monomer are required for polymer power quantities of 20, 40, 60 or 80 grams, respectively.

Although it was found that the various individual components can be mixed directly by hand, such mixing processes yield materials with poor homogeneity and stability and should therefore not be used.

Simple manual mixing of the required components for the preparation of the different modules, for example under operating room conditions or in the pharmacy, cannot satisfy the rigorous quality standards for an implant material. The pharmaceutically active agents or additives are frequently only available in preparations which cannot be homogeneously mixed with the starting materials. Manual mixing of implant materials and active agents and/or additives therefore poses certain risks and should be rejected.

Advantageously, the components 2 to 5 may already contain a fraction of the implant component 1 or of another implant material. This makes mixing much easier so that a homogeneous distribution of all components can be achieved even with short mixing times.

As observed in practice, homogeneous mixtures of active agents with the polymer powder of bone cements may be difficult to obtain even when using mortar and pestle. In particular, homogeneous mixtures may not be obtainable if the active agents are present in a coarse crystalline, severely porous or lyophilic form, if they form lumpy conglomerates, as for example with hygroscopic materials, or contain different sizes of hard particles with sharp edges.

Mixtures of this type exhibit inhomogeneities and defects in the hardened cement matrix and therefore significantly weaken the mechanical stability of the implant material. Moreover, the manually mixed compounds may not always be sterile.

According to the invention, when using modular implant components 2 to 5, the powdery or finely granulated components are thoroughly mixed together with a certain fraction of the material of the implant component 1 or another suitable implant material using a suitable mechanical mixing device, thereby homogeneously distributing the active agents(s) in the components. The mixing device can preferably be a mechanical tumbling mill or a positive mixer, preferably a fluidized bed mixer or a plow-shaped mixer. Such devices are known in the art. The mixing process can take place in a conventional manner and therefore need not be described in detail. It may be necessary, however, to mix the ingredients under cleanroom conditions.

According to the invention, an implant material can be prepared by mixing the modules 2 to 5 with at least one powdery or finely granulated basic material of the modular implant component 1, or another suitable implant material, and by adding a quantity of the active agents reflecting the intended dosage, before the material is further processed into a ready-to-use implant material, i.e., for example a bone cement powder based on polyacrylate or polymethacrylate, with or without active agents.

Surprisingly, it has been observed, for example, that the modular implant components 2 to 5 according to the invention can be homogeneously mixed with the basic implant component 1 simply by conventional, less harsh mixing by hand without additional aids. The quality of the total material is not degraded by concentration gradients. Mechanical mixing in a cement mixing system is also possible. A perfect and completely homogeneous mixture is also obtained by mixing in a prepackaged system or preferably in a vacuum mixing system, where the corresponding amount of polymer powder of the modular implant components 1 and/or the modular implant components 1, 2, 3, 4 or 5, or a mixture of different components of the modules 1-5 are added in advance of the actual mixing process.

The components for the ready-to-use implant material can be finally mixed in a sealed, especially constructed unit, for example a sterile single or multi-chamber system, or a suitable glass or metal container under atmospheric pressure or at a reduced pressure. The fraction of one or more components 1 to 5 in the modular implant component 1, which can be added to the mixing system first, is preferably 5 to 80 wt. %, preferably 10 to 50 wt. % with reference to the total weight of the implant material.

Bone cements mixed with the modular implant components 2 to 5 according to the invention are likewise produced by mixing one or more components of the modules 2 to 5 with a suitable bone cement polymer powder. The cement is readied for use by mixing the polymer powder mixture in a 2:1 ratio with a liquid monomer.

The produced modular implant components can be sterilized. Examination of different modular components has shown that not every sterilization method is suitable for every component. Different sterilization methods can be used depending on the properties of the components, for example gassing with ethylene oxide, sterilization with beta or gamma rays, to name some of the most frequently applied methods.

By preparing bone cements with the modular implant components according to the invention, pharmaceutically active agents, preferably antibiotics or additives, can be added to bone cements and other implant materials in an individually selected dose adapted to the clinical situation. The individual implant material produced in this way also satisfies the requirement for maintaining sterility, having a specific mixing characteristic and a homogeneous distribution of active agents with optimized and standardized release of the active ingredient from the hardened matrix, as well as retaining its mechanical properties. This provides a novel, beneficial and advantageous approach for dosing active agents for preparing implant materials containing such active agents, in particular bone cements.

The invention will be described hereinafter in more detail with reference to several examples.

EXAMPLE 1

For the Implant Component 2

10 kg of an arbitrary finely grained bone cement polymer powder are mixed in a plow-shaped mixer with 3 kg zirconium dioxide or barium sulfate, until the x-ray contrast material is homogeneously dispersed in the cement powder. Another type of mixer can be used for the mixing process.

EXAMPLE 2

For the Implant Component 2

The process is analogous to example 1, except that 10 kg polymer powder and 1 kg zirconium dioxide or barium sulfate are used.

EXAMPLE 3

For the Implant Component 2

The process is analogous to example 1, except that 10 kg polymer powder and 1 kg of a fine tantalum powder or another metal powder are used.

EXAMPLE 4

For the Implant Component 2

The process is analogous to example 1, except that 10 kg polymer powder and 3 kg of a fine hydroxyl apatite powder are used.

EXAMPLE 5

For the Implant Component 2

The process is analogous to example 1, except that 10 kg polymer powder and 5 kg of a fine hydroxyl apatite powder are used.

EXAMPLE 6

For the Implant Component 3

The process is analogous to example 1, except that 10 kg polymer powder and 1 kg gentamycin are used.

EXAMPLE 7

For the Implant Component 3

The process is analogous to example 1, except that 10 kg polymer powder and 500 g gentamycin are used.

EXAMPLE 8

For the Implant Component 3

The process is analogous to example 1, except that 10 kg polymer powder and 2 kg gentamycin are used.

EXAMPLE 9

For the Implant Component 3

The process is analogous to example 1, except that 10 kg polymer powder and 1 kg clindamycin are used.

EXAMPLE 10

For the Implant Component 3

The process is analogous to example 1, except that 10 kg polymer powder and 500 g methotrexate are used.

EXAMPLE 11

For the Implant Component 3

The process is analogous to example 1, except that 10 kg polymer powder and 2 kg ampicillin or teichoplanin or vancomycin or other antibiotics are used.

EXAMPLE 13

For the Implant Component 4

The process is analogous to example 1, except that 10 kg polymer powder and 3 kg of another polymer powder are used, whose copolymer has a higher molecular weight and a significantly greater modulus of elasticity.

EXAMPLE 14

For the Implant Component 4

The process is analogous to example 1, except that 10 kg polymer powder and 5 kg of another polymer powder are used, whose copolymer has a higher molecular weight and a significantly greater modulus of elasticity.

EXAMPLE 15

For the Implant Component 5

The process is analogous to example 1, except that 10 kg polymer powder and 5 kg of another polymer powder are used, whose copolymer has a rapid swelling characteristic and a low viscosity.

EXAMPLE 16

For the Implant Component 5

The process is analogous to example 1, except that 10 kg polymer powder and 5 kg of another polymer powder are used, whose copolymer has a slow swelling characteristic and a high viscosity.

EXAMPLE 17

For Use of an Implant Component in a Bone Cement

A modular implant component according to one of the examples 1-16 is sterilized by gassing or irradiation and mixed in a ratio 1+3, 2+2 or 3+1 parts with a sterile bone cement polymer powder which may or may not contain active agents or additives, of the type used for producing the modular implant components, or with an arbitrary bone cement powder. Mixing is done in a suitable mixing system in which the bone cement polymer powder is placed, preferably under reduced atmospheric pressure, intermediately before application. For readying the cement, the polymer powder mixture is mixed in a proportion of approximately 40 g solid material to 20 ml liquid monomer.

Additional examples will be evident to those skilled in the art from the above description.

The invention claimed is:

1. A modular implant system for preparing an individualized patient-specific implant application comprising
a first implant component consisting of bone cement made of one or more materials selected from the group consisting of powdery or finely granular polyacrylates, powdery or finely granular polymethacrylates, and a polymerization catalyst, without the presence of active agents, and
a second implant component in powdery or finely granular form and comprising the bone cement of the first implant component and at least one powdery or finely granular active pharmaceutical agent and/or an additive,
wherein the at least one powdery or finely granular active pharmaceutical agent and/or the additive is present in the second implant component at a concentration of at least about twice as high as a dose required for a final clinical application.

2. The modular implant system according to claim 1, wherein the at least one active pharmaceutical agent or the additive is a chemotherapeutical agent.

3. The modular implant system according to claim 1, wherein the at least one active pharmaceutical agent or the additive is an antibiotic agent.

4. The modular implant system according to claim 3, wherein the antibiotic agent is selected from the group consisting of amino glycoside-antibiotics, β-lactam-antibiotics, clindamycin, vancomycin, teichoplanin, and rifapicin.

5. The modular implant system according to claim 2, wherein the chemotherapeutical agent is methotraxate.

6. The modular implant system according to claim 1, wherein the at least one active pharmaceutical agent or the additive comprises two different pharmaceutical active agents or additives.

7. The modular implant system according to claim 1, wherein grain sizes of the powdery or finely granular polyacrylates and/or polymethacrylates are substantially the same as grain sizes of the at least one powdery or finely granular active pharmaceutical agent and/or the additive.

8. The modular implant system according to claim 1, further comprising a liquid monomer component.

9. The modular implant system according to claim 1, wherein the proportion of the first implant component or the second implant component is 5 to 80 wt. % referenced to the total weight of the modular implant system.

10. The modular implant system according to claim 9, wherein the proportion of the first implant component and the second implant component is 10 to 50 wt. %, referenced to the total weight of the modular implant system.

11. The modular implant system according to claim 8 wherein the liquid monomer component, the first implant component and the second implant component are mixed in a sealed unit.

12. The modular implant system according to claim 1, wherein the second implant component comprises an x-ray contrast material as the additive.

13. The modular implant system according to claim 12, wherein the x-ray contrast material is selected form the group consisting of barium sulfate, zirconium dioxide, hydroxyl apatite and tantalum.

14. A method for producing an implant material for a modular implant system comprising the steps of
providing a first implant component consisting of bone cement made of one or more materials selected from the group consisting of powdery or finely granular polyacrylates, powdery or finely granular polymethacrylates and a polymerization catalyst, without the presence of active agents, and
providing a second implant component in powdery or finely granular form and comprising the bone cement of the first implant component and at least one active pharmaceutical agent and/or additive, wherein the at least one active pharmaceutical agent and/or the additive is present in the second implant component at a concentration of at least about 30% higher than a dose required for a final clinical application; and
thoroughly mixing the first implant component and the second implant component in a sealed mixing device.

15. The method according to claim 14, wherein the sealed mixing device is selected from a group consisting of mechanical tumbling mill, a positive mixer, and a fluidized bed mixer.

16. The method according to claim 14, wherein the first and the second implant components are sterilized before being mixing.

17. The method according to claim 14, wherein the sterilization is accomplished by gassing with ethylene oxide or by irradiation.

18. The method according to claim 17, wherein the mixing of the components is performed in a sterile plastic or glass container.

19. The modular implant system according to claim 1, wherein the bone cement further comprises a fine-particle pre-polymer containing a polymerization catalyst.

20. A modular implant system for preparing an individualized patient-specific implant application comprising:
a first implant component consisting of bone cement made of one or more materials selected from the group consisting of polyacrylates, polymethacrylates and a polymerization catalyst, without the presence of active agents; and
a second implant component comprising the bone cement of the first implant component and at least one implant component comprising at least one active pharmaceutical agent and/or additive,
wherein the at least one active pharmaceutical agent and/or the additive is present in the second implant component at a concentration of at least about 30% higher than a dose required for a final clinical application, and further wherein the modular implant system consists of ingredients in powdery or finely granular form.

* * * * *